United States Patent [19]

Ruiz

[11] Patent Number: 5,954,765
[45] Date of Patent: Sep. 21, 1999

[54] SELF-ADJUSTING PROSTHESIS FOR TREATING CONSTRICTIONS IN GROWING VESSELS

[76] Inventor: Carlos E. Ruiz, 1747 N. Country La., Pasadent, Calif. 91107

[21] Appl. No.: 08/963,561

[22] Filed: Nov. 3, 1997

[51] Int. Cl.⁶ ..................................................... A61F 2/06
[52] U.S. Cl. ............................................... 623/1; 606/194
[58] Field of Search ......................... 623/1, 12; 606/108, 606/192, 194, 195

[56] References Cited

U.S. PATENT DOCUMENTS

| | | | |
|---|---|---|---|
| 4,655,771 | 4/1987 | Wallsten | 623/1 |
| 4,665,918 | 5/1987 | Garza et al. | 128/343 |
| 4,733,665 | 3/1988 | Palmaz | 128/343 |
| 4,877,030 | 10/1989 | Beck et al. | 128/343 |
| 5,067,957 | 11/1991 | Jervis | 606/108 |
| 5,100,429 | 3/1992 | Sinofsky et al. | 606/195 |
| 5,192,307 | 3/1993 | Wall | 623/1 |
| 5,306,294 | 4/1994 | Winston et al. | 623/1 |
| 5,354,309 | 10/1994 | Schnepp-Pesch et al. | 606/198 |
| 5,383,926 | 1/1995 | Lock et al. | 623/1 |
| 5,441,515 | 8/1995 | Khosravi et al. | 606/194 |
| 5,607,445 | 3/1997 | Summers | 606/198 |
| 5,632,771 | 5/1997 | Boatman et al. | 623/1 |
| 5,643,314 | 7/1997 | Carpenter et al. | 606/198 |
| 5,649,977 | 7/1997 | Campbell | 623/1 |
| 5,733,328 | 3/1998 | Fordenbacher | 623/1 |
| 5,735,871 | 4/1998 | Sgro | 606/198 |

*Primary Examiner*—David H. Willse
*Assistant Examiner*—Bruce E. Snow
*Attorney, Agent, or Firm*—Fish & Neave; Nicola A. Pisano

[57] ABSTRACT

A prosthesis for treating congenital defects and constrictive diseases in pediatric cases is provided that self-adjusts to accommodate growth of the vessel as the child matures. The prosthesis includes a plurality of spaced apart, self-adjusting, tapered support members that extend from an interconnection member. The prosthesis preferably comprises a nickel-titanium material that exhibits pseudo-elastic behavior at body-temperature, so as to apply an approximately uniform stress to the vessel over a range of expanded diameters. The interconnection member and/or a subset of the support members may include portions defining windows that assist in anchoring the prosthesis within a vessel. Methods of implanting the prosthesis are also provided.

20 Claims, 4 Drawing Sheets

SELF-ADJUSTING PROSTHESIS FOR TREATING CONSTRICTIONS IN GROWING VESSELS

FIELD OF THE INVENTION

The present invention relates to apparatus and methods for treating congenital defects and pediatric constrictive diseases. More particularly, the present invention provides an endoluminal prosthesis, and methods of use, for treating pediatric congenital defects or disease-related constrictions wherein the prosthesis self-adjusts to accommodate growth in the vessel diameter as the child grows.

BACKGROUND OF THE INVENTION

Each year several thousand children are born with congenital heart defects, such as pulmonary artery branch stenosis, coarctation of the aorta, and bilateral renal stenosis. Pulmonary artery branch stenosis results from underdevelopment of the pulmonary arteries, and causes a narrowing of the arteries that reduces blood flow to the lungs. It may also occur as a consequence of a previous palliative surgical procedure. Coarctation of the aorta likewise results from underdevelopment of portions of the aorta, and causes constrictions in the aorta that reduce blood flow to the extremities and adversely impact heart function. Similarly, bilateral renal stenosis, caused by underdevelopment of the renal arteries, can lead to reduced kidney function and hypertension.

An aspect common to all of the foregoing congenital diseases, as well as other pediatric constrictive diseases, is that the arteries subject to the disease grow rapidly during the early years of a child's life. For example, the pulmonary artery in an infant may double in size within the first twelve months, and continues to increase in diameter throughout the first decades of the child's life.

Previously known endoprostheses, such as those described in U.S. Pat. No. 4,733,665 to Palmaz, and U.S. Pat. No. 4,655,771 to Wallsten, are capable of only a limited range of expansion. Once such endoprostheses are deployed, they do not possess the capability to freely expand with the vessel diameter as the child grows. In particular, due to the fixed diameter of such endoprostheses, somatic growth causes the vessel to become relatively stenotic. For example, the stent described in the patent to Palmaz is incapable of self-expanding, while the stent described in the patent to Wallsten is capable of only a limited degree of radial expansion, once deployed.

While other previously known endoprostheses have been proposed, none appear suitable for use in treating congenital constrictive disease in pediatric patients. Coiled sheet stents, such as described in U.S. Pat. No. 5,306,294 Winston et al., do not possess the necessary flexibility to permit deployment through tortuous anatomy. Some stents, such as described in U.S. Pat. No. 5,441,515 to Khosravi et al. and U.S. Pat. No. 5,643,314 to Carpenter et al., provide for positive locking of the stent at a selected diameter, thereby inhibiting future expansion as the vessel grows.

Other stents, such as coil spring stents, e.g., as described in U.S. Pat. No. 4,665,918 to Garza et al., do not appear to possess the necessary resiliency to undergo the diameter changes. Instead, the coil-spring structure described in that patent–and present in most other coil-spring type stents— tends to promote tissue growth through the gaps of the coil. Consequently, such devices tend to become ingrown in the vessel wall, and may act as a permanent constriction in the vessel, rather than expanding as the vessel diameter increases. The drawback of tissue ingrowth is similarly expected to pose a problem with other stent designs. For example, the locking lugs of the stent described in U.S. Pat. No. 5,192,307 to Wall are likewise expected to engage the vessel wall and become ingrown, thereby inhibiting further expansion of the stent.

In view of the foregoing, it would be desirable to provide a prosthesis, and methods of use, suitable for use in treating congenital defects and constrictive disease wherein the device is capable of expanding to self-adjust to the growth of the vessel.

It further would be desirable to provide a prosthesis, suitable for treating congenital defects and constrictive disease, that retains its ability to support a vessel wall as the vessel diameter expands, with reduced risk of migration.

It still further would be desirable to provide a prosthesis capable of self-adjusting to a growing vessel which is designed to reduce tissue ingrowth that could restrict the capability of the prosthesis to expand in diameter as the vessel grows.

It also would be desirable to provide apparatus and methods suited for percutaneous delivery of a prosthesis capable of self-adjusting to accommodate a growing vessel.

SUMMARY OF THE INVENTION

In view of the foregoing, it is an object of this invention to provide a prosthesis, and methods of use, suitable for use in treating congenital defects and constrictive disease wherein the device is capable of expanding to self-adjust to the growth of the vessel.

It is another object of the present invention to provide a prosthesis, suitable for treating congenital defects and constrictive disease, that retains its ability to support a vessel wall as the vessel diameter expands, with reduced risk of migration.

It is a further object of the invention to provide a prosthesis capable of self-adjusting to a growing vessel which is designed to reduce tissue ingrowth that could restrict the capability of the prosthesis to expand in diameter as the vessel grows.

It is a still further object of this invention to provide apparatus and methods suited for percutaneous delivery of a prosthesis capable of self-adjusting to accommodate a growing vessel.

These and other objects of the present invention are accomplished by providing a prosthesis having a plurality of self-adjusting support members suitable for maintaining the patency of a constricted vessel. In accordance with present invention, the prosthesis is capable of continuously maintaining contact with, and supporting, the vessel wall as the child grows.

In a preferred embodiment, the prosthesis comprises a plurality of support members extending from an interconnection member. When implanted in a vessel, the interconnection member is generally aligned with a longitudinal axis of the vessel, while a tip of each of the plurality of support members overlaps its base portion to form a ring. The prosthesis preferably comprises a nickel-titanium material which is alloyed to exhibit pseudo-elastic behavior at body-temperature. Accordingly, the stress applied by the prosthesis, when implanted, is expected to remain approximately constant throughout the expected range of expanded diameters of the prosthesis.

In addition, each support member of the prosthesis preferably is tapered from base to tip, to enhance the ability of the support member to self-expand as the vessel grows. The support members may, in addition, be coated with an optional biocompatible substance that inhibits tissue growth, thereby reducing the risk that the prosthesis will become ingrown in the vessel wall.

Methods of percutaneously implanting a prosthesis constructed in accordance with the present invention are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides a prosthesis, and methods of use, for treating congenital and disease-related narrowing of vessels in children. A prosthesis constructed in accordance with the present invention is capable of maintaining the patency of a constricted portion of a vessel, and self-adjusts to continually support the vessel as the child grows. The prosthesis preferably is structurally designed to reduce tissue ingrowth that might interfere with the self-adjusting capability of the prosthesis, and may also include a biocompatible coating to further inhibit tissue ingrowth.

It is expected that prostheses constructed in accordance with the present invention will find a wide variety of applications in treating constrictive disease in pediatric cases, including such congenital defects as pulmonary artery branch stenosis, coarctation of the aorta, and renal stenosis.

Figure 1A:
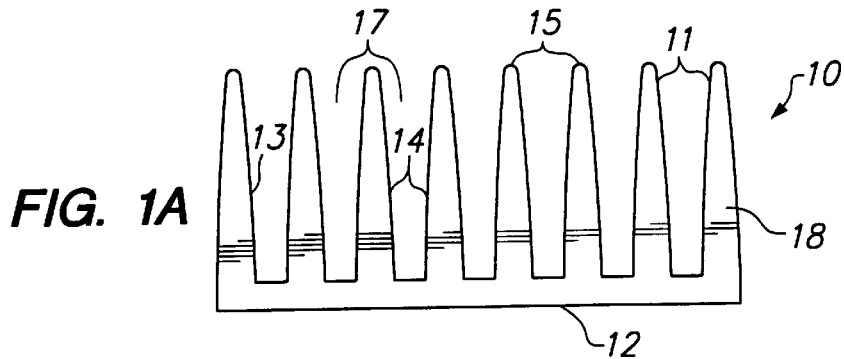
FIGS. 1A and 1B are, respectively, a plan and perspective view of a first embodiment of a prosthesis constructed in accordance with the present invention.
Figure 1B:
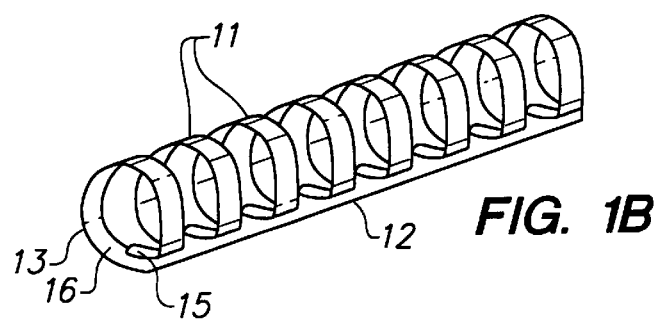

Referring to FIGS. 1A and 1B, a first embodiment of prosthesis 10 constructed in accordance with the present invention is described. Prosthesis 10, shown spread flat in FIG. 1A, comprises a plurality of spaced apart support members 11 extending at intervals from interconnection member 12. Each support member 11 includes base portion 13, atraumatic tip 15, and tapered portion 14 extending between base portion 13 and tip 15. As shown in FIG. 1B, prosthesis 10 is rolled about a longitudinal axis aligned with interconnection member 12, so that support members 11 form approximately circular rings and tips 15 of support members 11 are disposed against interior surfaces 16 of base portions 13. Gaps 17 between adjacent support members 11 provide longitudinal flexibility to prosthesis 10, thus enabling it to pass through tortuous anatomy.

Prosthesis 10 preferably comprises a resilient material, such as a stainless steel alloy, biocompatible polymer, or nickel-titanium alloy, and more preferably comprises a nickel-titanium material alloyed to exhibit pseudo-elastic behavior when implanted in a patient's vessel. Pseudo-elastic nickel-titanium alloys have been suggested for use in variety of medical devices because such alloys are known to apply a uniform stress over a wide range of strains, as described, for example, in U.S. Pat. No. 5,067,957 to Jervis (See column 10 at lines 7–24).

Alternatively, the prosthesis 10 may comprise a wire mesh frame covered with a biocompatible material that prevents tissue ingrowth through the mesh. Thus, for example, the frame may be formed from a resilient and self-expanding material, such nickel-titanium, and include a coating of biocompatible material, for example, polytetrafluoroethylene (PTFE) sintered or glued to its outer surface.

In accordance with the present invention, tips 15 of support members 11 are biased to expand radially outwardly. In this manner, when the vessel diameter increases as the child grows, the prosthesis self-adjusts by expanding an equal amount, thereby continuously maintaining the patency of the vessel. In particular, each support member 11 is wound so that its tip 15 overlaps its respective base portion 13. Thus, as the vessel diameter increases, tip 15 slides circumferentially along the interior of its respective base portion, causing the diameter of the ring formed by the support member to increase to accommodate the larger vessel diameter.

Moreover, since support members 11 preferably are tapered from tip to base, tissue ingrowth into gaps 17 does not impede outward expansion of the rings as the vessel diameter increases. To ensure that the support members remain free to expand with the growing vessel, support members 11 do not have any outward projections that might become embedded in the vessel wall and impede free radial movement of tips 15. In addition, prosthesis 10 may include coating 18 of a biocompatible substance, e.g., polytetrafluoroethylene, that retards tissue ingrowth into gaps 17. Coating 18 may alternatively take the form of a suitable drug impregnated polymer. Alternatively, or in addition, the exterior surfaces of prosthesis 10 may be finished to provide a smooth surface that improves sliding of the support members relative to the vessel wall.

Figures 2A, 2B, 2C:
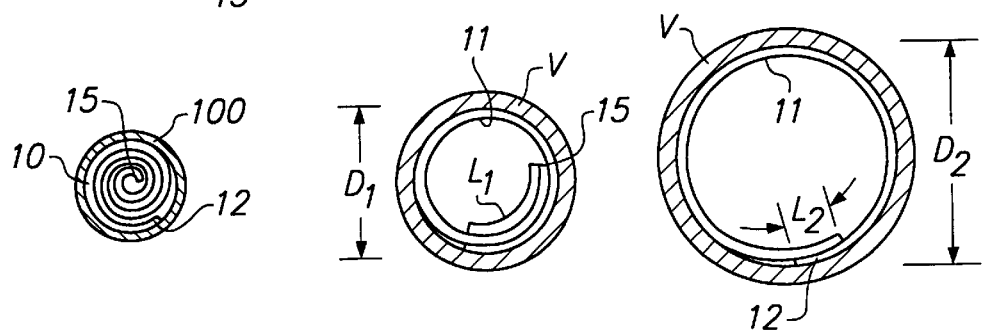
FIGS. 2A, 2B and 2C are end views of the prosthesis of FIG. 1 in its contracted delivery state, after implantation, and several months after implantation, respectively.

Referring now to FIG. 2A, prosthesis 10 is shown coiled to contracted delivery state within outer sheath 100 of a delivery device. In accordance with the methods of the present invention, prosthesis 10 is wound to a coil along a longitudinal axis aligned with interconnection member 12, so that support members 11 form a series of coils and interconnection member 12 is disposed along the outermost edge of the coil. Prosthesis 10 is then loaded into a delivery device from which it may be deployed by holding the prosthesis stationary and withdrawing outer sheath 100. An illustrative delivery device suitable for use with the present invention is described in the above-mentioned U.S. patent to Garza et al.

In FIG. 2B, prosthesis 10 is depicted deployed in an infant, at time $T_1$, in vessel V having diameter $D_1$. In this state, tip 15 of support member 11 overlaps base portion 13 of its respective support member by an arc length $L_1$. In FIG. 2C, prosthesis 10 is depicted at time $T_2$, several months or years after time $T_1$ as having expanded diameter $D_2$. In this state, the amount of overlap of tip 15 with its base portion has been reduced to arc length $L_2$, while the overall circumference of the prosthesis has grown. Applicant expects that the length of support members 11 may be selected to have an initial arc length of overlap after deployment to accommodate expansion of the prosthesis throughout the useful lifetime of the device. Alternatively, the length of support member 11 may be selected so that a gap eventually opens between tip 15 and interconnection member 12.

Figure 3A:
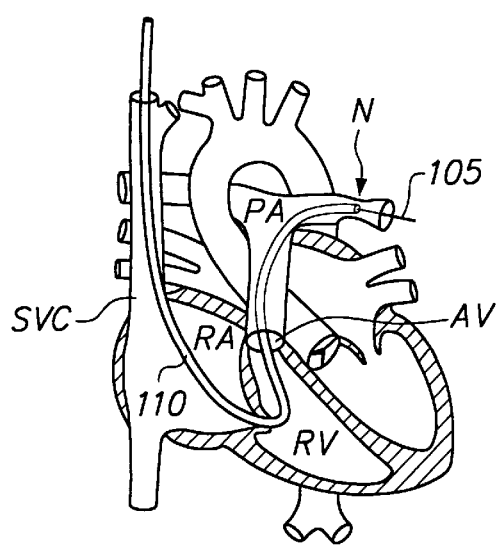
FIGS. 3A and 3B depict steps in an illustrative method of deploying the prosthesis of FIG. 1 in a narrowed portion of a pulmonary artery.
Figure 3B:
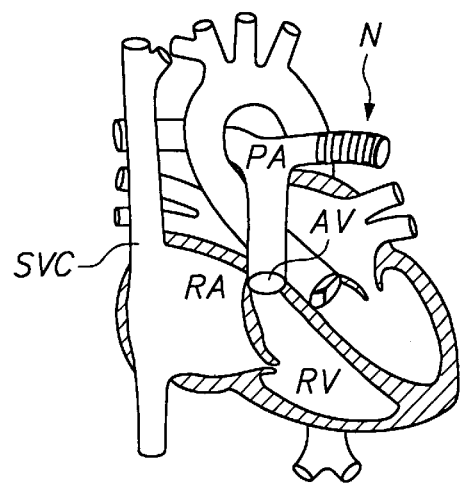

With respect to FIGS. 3A and 3B, percutaneous deployment of prosthesis 10 is described for use in treating pulmonary artery branch stenosis. In FIG. 3A, delivery device 110 is shown disposed in the left pulmonary artery. Using conventional interventional cardiology techniques, guide wire 105 is first disposed in patient's pulmonary artery by inserting the guide wire via the subclavian vein through the superior vena cava SVC (or via a femoral vein and the inferior vena cava), right atrium RA, right ventricle RV and pulmonary artery PA. A previously known dilatation device (not shown), e.g., an angioplasty balloon, may then be inserted within narrowed region N and inflated to disrupt the stenosis or enlarge the vessel.

Delivery device 110 is then advanced along guide wire 105 so that prosthesis 10 is aligned with narrowed region N in the left pulmonary artery, as determined by fluoroscopy and, for example, a radio-opaque marker disposed on the delivery device or prosthesis 10. Once the prosthesis is disposed at a desired location, outer sheath 100 is withdrawn, allowing prosthesis 10 to uncoil into contact with the vessel wall to maintain the patency of the vessel, as shown in FIG. 3B. The delivery device and guide wire are then withdrawn. As described hereinabove, prosthesis 10 continuously exerts a radially outward force against the vessel wall, even when the vessel enlarges as the child grows.

Figure 4A:
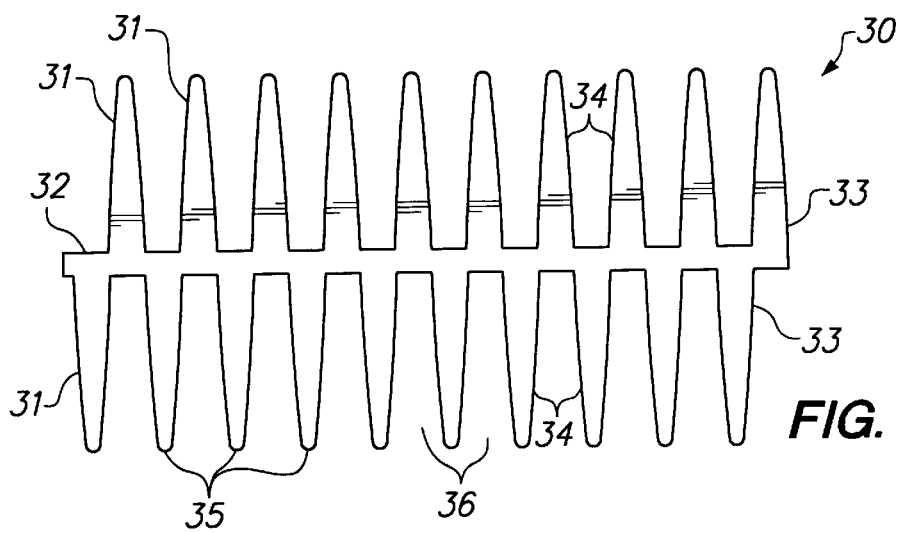
FIGS. 4A and 4B are, respectively, plan and partial perspective views of an alternative embodiment of a prosthesis constructed in accordance with the present invention.
Figure 4B:
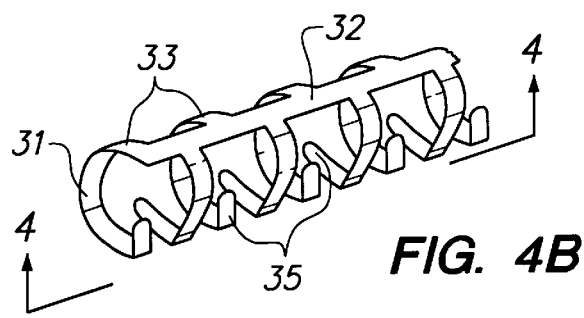

Referring now to FIG. 4A, an alternative embodiment of the prosthesis of the present invention is described. Prosthesis 30 is similar to that of FIGS. 1A and 1B, but includes a plurality of support members 31 extending from either side of interconnection member 32. Each support member 31 preferably includes base portion 33 joined to atraumatic tip 35 by tapered portion 34, as described hereinabove with respect to prosthesis 10. When configured in its deployed state, prosthesis 30 assumes the shape depicted in FIG. 4B, with support members biased radially outward.

Figure 4C:
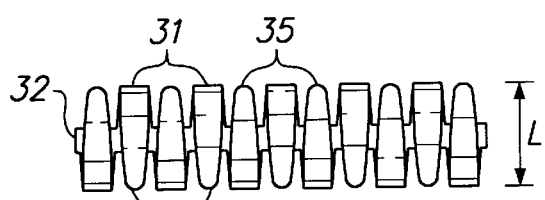
FIGS. 4C and 4D depict a view of the stent taken along view line 4—4 at two different times after implantation of the device.
Figure 4D:
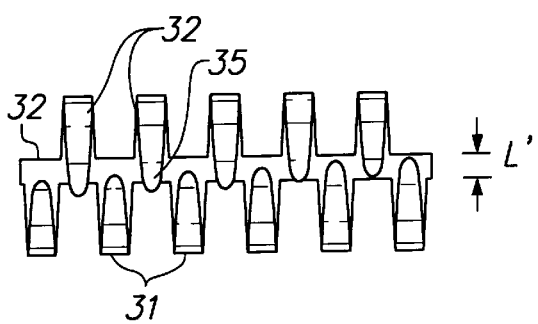

Referring to FIGS. 4C and 4D, prosthesis 30 is shown at times $T_1$ and $T_2$, respectively after implantation in a vessel. In FIG. 4C, prosthesis 30 is shown at time $T_1$, soon after deployment, where support members 31 are tightly interdigitated and overlap by an arc length L (measured as the arc length from the tip of the support members on one side of interconnection member 32 to the tip of the support members on the opposing side). In FIG. 4D prosthesis 30 is shown at time $T_2$, long after initial deployment. At time $T_2$, prosthesis 30 has expanded radially to accommodate the growth of the vessel and support members 31 consequently overlap by a smaller arc length L'. It is contemplated that support members 31 will generate sufficient radially outwardly directed force to maintain the vessel patent, without having tips 35 overlap base portions 33. Alternatively, the use of longer support members providing such overlap may be advantageous in some clinical applications.

Figure 4E:
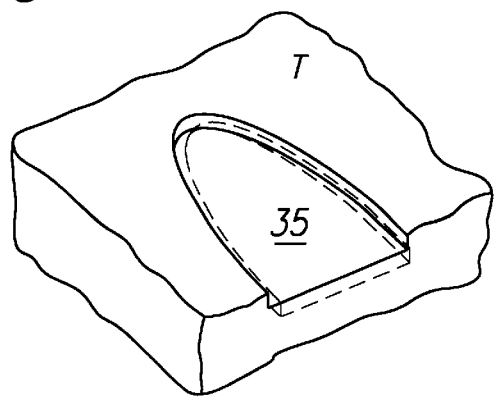
FIG. 4E illustrates movement of the support member relative to ingrown tissue as a support member expands radially.

As in the embodiment of FIGS. 1A and 1B, it is expected that for prosthesis 30 the taper of tapered portions 34 will enable support members 31 to slide freely to accommodate growth in the vessel diameter, without being impeded by tissue ingrowth. In particular, because the thickness of the tapered portion decreases as the support member uncoils, any tissue that has grown into gaps 36 should pose little mechanical resistance. This feature is illustrated in FIG. 4E, wherein the solid outline of tip 35 reflects the edge of tissue T growing into gap 36 at time $T_1$, and the dotted line illustrates the edge of the tissue T at time $T_2$, when the prosthesis has radially expanded and tip 35 has been displaced.

Figure 5A:
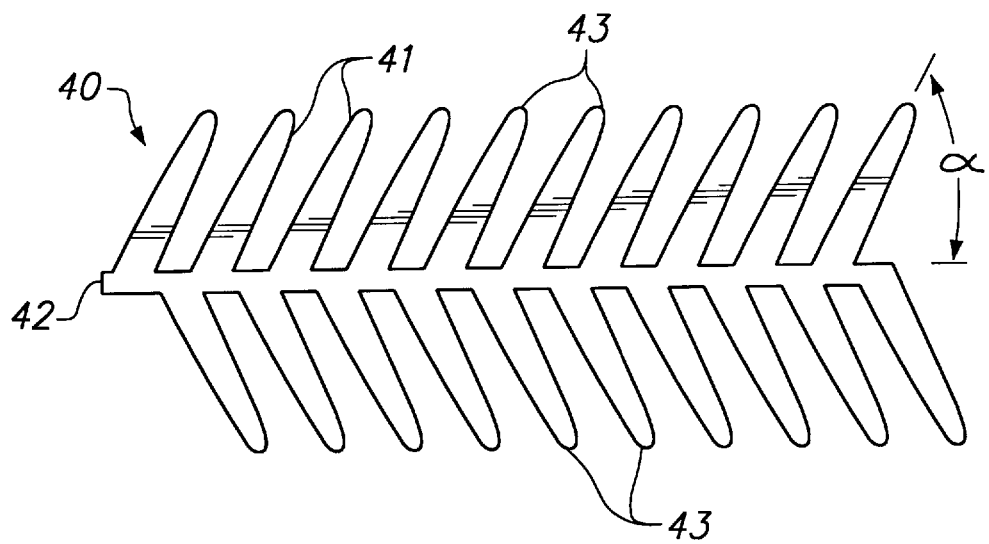
FIGS. 5A to 5C are views similar to those of FIGS. 4A–4C for another alternative embodiment of a prosthesis constructed in accordance with the present invention.
Figure 5B:
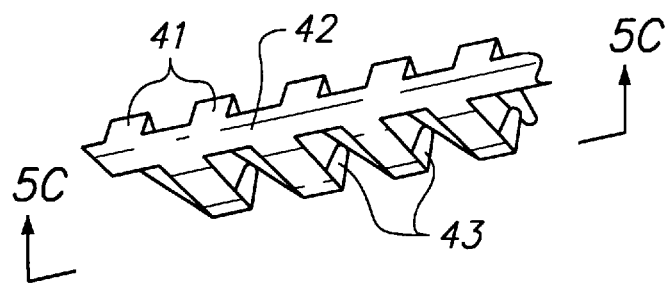
Figure 5C:
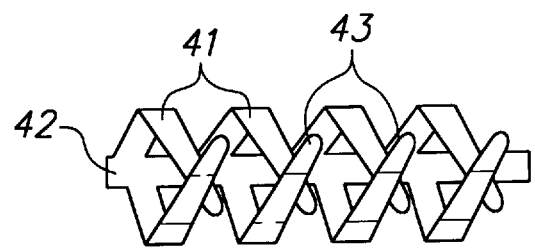

Referring now to FIGS. 5A to 5C, a yet further alternative embodiment of the prosthesis of the present invention is described. Prosthesis 40 is similar in construction to prosthesis 30 of FIGS. 4A–4E, except that support members 41 are not orthogonal to interconnection member 42, but instead form an angle α. In one preferred embodiment, a forms an angle of about 75°. When rolled along a longitudinal axis aligned with interconnection member 42, prosthesis 40 assumes the shape illustrated in FIG. 5B, wherein tips 43 of alternating support members 41 overlap, as best seen in FIG. 5C. Support members 41 preferably are tapered from base to tip as described hereinabove, and enable the prosthesis to freely expand to accommodate growth of the vessel in which the prosthesis is deployed. Prosthesis 40 is deployed in accordance with the methods and using the apparatus described hereinabove.

Figure 6A:
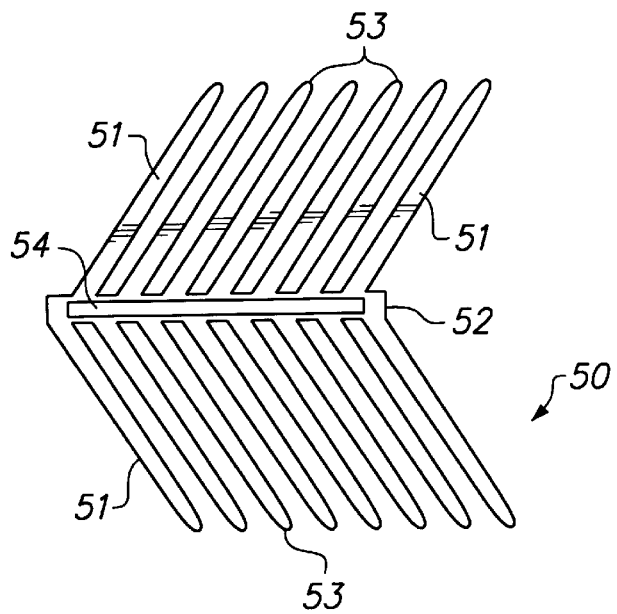
FIGS. 6A to 6C are views similar to FIG. 1A for various alternative embodiments of a prosthesis constructed in accordance with the present invention.
Figure 6B:
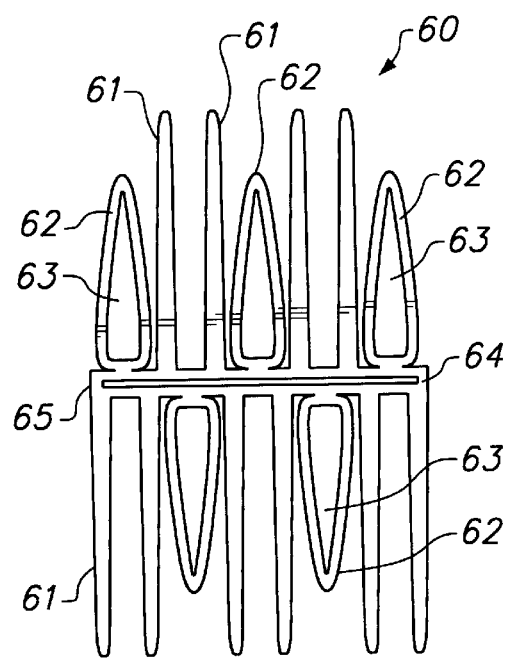
Figure 6C:
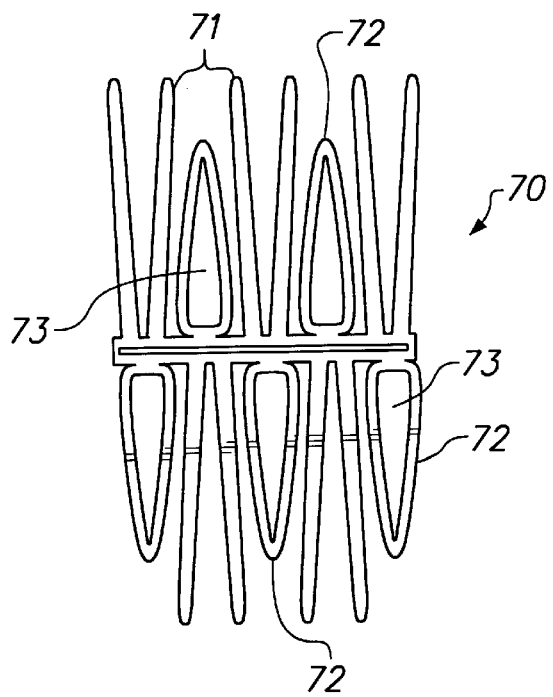

Referring now to FIGS. 6A to 6C, additional embodiments 50, 60 and 70 of the prosthesis of the present invention are shown. Prosthesis 50 is similar in appearance and construction to prosthesis 40 of FIG. 5A, and includes support members 51 projecting from interconnection member 52. Support members 51 are tapered from tips 53 to the point of attachment to interconnection member 52. Prosthesis 50 is illustratively formed of a nickel-titanium wire mesh having a non-porous biocompatible coating or covering attached to at least the outer surface of the wire mesh.

Prosthesis 50, however, differs from prosthesis 40 in that prosthesis 50 includes slot 54 formed in interconnection member 52. Applicant expects that after deployment of prosthesis 50, tissue will grow through slot 54 and anchor the prosthesis in position along its length. Thus, while support members 51 are configured to permit expansion of the prosthesis to accommodate growth of the vessel, slot 54 provides at least one point of attachment of the prosthesis to the vessel wall.

Prosthesis 60 of FIG. 6B provides a further alternative configuration of the self-adjusting prosthesis of the present invention. Prosthesis 60 includes tapered support members 61 alternating with reduced-length support members 62 having windows 63. Support members 61 and 62 are connected to interconnection member 64. As in the embodiment of FIG. 6A, interconnection member 64 includes slot 65 that serves to anchor the prosthesis within the vessel. In addition, windows 63 of reduced-length support members 62 also permit tissue growth through those members.

Accordingly, the prosthesis of FIG. 6B will become anchored not only along its length via tissue growth through slot 65, but also partly in the circumferential direction as well via tissue growth through windows 63. Applicant expects that this arrangement will reduce the risk of migration of the prosthesis, while providing a device that is capable of self-expanding to adjust to growth of the circumference of the vessel.

In FIG. 6C, prosthesis 70 illustrates an alternative embodiment of the prosthesis of FIG. 6B. In prosthesis 70, support members 71 project away from interconnection at different angles. In prosthesis 70, reduced-length support members 72 having windows 73 alternate with pairs of support members 71. As will of course be apparent to one of skill in the art of endoprosthesis design, any number of support members may be interposed between adjacent reduced-length support members.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A prosthesis for deployment in a vessel to treat pediatric congenital defects and constrictive diseases, the prosthesis comprising:
    an interconnection member defining a longitudinal axis, the interconnection member having a portion defining a longitudinally-oriented slot, the longitudinally-oriented slot enabling tissue to grow therethrough to anchor the prosthesis within the vessel; and
    a plurality of support members extending in a direction away from the longitudinal axis, each one of the support members having a base portion adjoined to the interconnection member, an atraumatic tip, and being tapered from a first width at the base portion to a second width at the tip, the second width smaller than the first width,
    the prosthesis having a first deployed state, at the time of initial deployment, wherein the support members expand radially to a first diameter to support the vessel, and a second deployed state, temporally remote from time of initial deployment and after growth of the vessel, wherein the support members expand to a second diameter, larger than the first diameter, to support the vessel.

2. The prosthesis as defined in claim 1 wherein the support members are inclined at an angle $\alpha$ with respect to the longitudinal axis.

3. The prosthesis as defined in claim 1 wherein the interconnection member has first and second lateral faces and the plurality of support members all project from the first lateral face.

4. The prosthesis as defined in claim 3 wherein each base portion has an interior surface and the tip of each support member overlaps the interior surface of the base portion by a predetermined amount.

5. The prosthesis as defined in claim 3 wherein alternating ones of the plurality of support members extend from the first and second lateral faces of the interconnection member, respectively.

6. The prosthesis as defined in claim 5 wherein the alternating ones of the plurality of support members are interdigitated in at least the first deployed state.

7. The prosthesis as defined in claim 1 wherein prosthesis comprises a nickel-titanium alloy that exhibits pseudo-elastic behavior at body temperature.

8. The prosthesis as defined in claim 1 further comprising a coating of biocompatible material extending between the support members to inhibit tissue ingrowth between the support members.

9. The prosthesis as defined in claim 1 wherein a subset of the plurality of support members are of reduced length and include portions defining windows.

10. The prosthesis as defined in claim 1 wherein the interconnection member and the plurality of support members comprise a wire mesh formed of a shape memory alloy, the wire mesh covered with a non-porous biocompatible material.

11. A prosthesis for deployment in a vessel to treat pediatric congenital defects and constrictive diseases, the prosthesis comprising:
    a wire mesh formed of a shape memory alloy comprising:
        an interconnection member defining a longitudinal axis; and
        a plurality of support members extending in a direction away from the longitudinal axis, each one of the support members having a base portion adjoined to the interconnection member, an atraumatic tip, and being tapered from a first width at the base portion to a second width at the tip, the second width smaller than the first width; and
    a non-porous biocompatible material disposed on the wire mesh,
    the prosthesis having a first deployed state, at the time of initial deployment, wherein the support members expand radially to a first diameter to support the vessel, and a second deployed state, temporally remote from time of initial deployment and after growth of the vessel, wherein the support members expand to a second diameter, larger than the first diameter, to support the vessel.

12. The prosthesis as defined in claim 11 wherein the support members are inclined at an angle $\alpha$ with respect to the longitudinal axis.

13. The prosthesis as defined in claim 11 wherein the interconnection member has first and second lateral faces and the plurality of support members all project from the first lateral face.

14. The prosthesis as defined in claim 13 wherein each base portion has an interior surface and the tip of each support member overlaps the interior surface of the base portion by a predetermined amount.

15. The prosthesis as defined in claim 13 wherein alternating ones of the plurality of support members extend from the first and second lateral faces of the interconnection member, respectively.

16. The prosthesis as defined in claim 15 wherein the alternating ones of the plurality of support members are interdigitated in at least the first deployed state.

17. The prosthesis as defined in claim 11 wherein prosthesis comprises a nickel-titanium alloy that exhibits pseudo-elastic behavior at body temperature.

18. The prosthesis as defined in claim 11 further comprising a coating of biocompatible material extending between the support members to inhibit tissue ingrowth between the support members.

19. The prosthesis as defined in claim 11 wherein the interconnection member has a portion defining a longitudinally-oriented slot, the longitudinally-oriented slot enabling tissue to grow therethrough to anchor the prosthesis within the vessel.

20. The prosthesis as defined in claim 11 wherein a subset of the plurality of support members are of reduced length and include portions defining windows.

* * * * *